United States Patent
Ishikawa et al.

[11] Patent Number: 5,982,172
[45] Date of Patent: Nov. 9, 1999

[54] METHOD OF DETECTING PLASTIC DEFORMATION IN STEEL USING A DIFFERENTIAL TYPE MAGNETIC FIELD SENSOR

[75] Inventors: Noboru Ishikawa; Hiroshi Yamakawa, both of Tokyo; Kazuo Chinone, Chiba; Satoshi Nakayama, Chiba; Akikazu Odawara, Chiba, all of Japan

[73] Assignee: Seiko Instruments Inc., Chiba, Japan

[21] Appl. No.: 08/746,794

[22] Filed: Nov. 15, 1996

[30] Foreign Application Priority Data

Nov. 17, 1995 [JP] Japan ................... 7-300276

[51] Int. Cl.⁶ ............. G01B 7/24; G01N 27/82; G01R 33/12
[52] U.S. Cl. ............. 324/209; 324/241; 324/260
[58] Field of Search ............. 324/209, 240–242, 324/244, 248, 260; 73/779

[56] References Cited

U.S. PATENT DOCUMENTS

| | | | |
|---|---|---|---|
| 4,503,393 | 3/1985 | Moyer et al. | |
| 4,528,856 | 7/1985 | Junker et al. | 324/209 X |
| 4,755,753 | 7/1988 | Chern | 324/240 X |
| 5,166,614 | 11/1992 | Yokosawa et al. | 324/248 |
| 5,293,119 | 3/1994 | Podney | 324/248 X |
| 5,331,278 | 7/1994 | Evanson et al. | 3245/248 X |
| 5,418,363 | 5/1995 | Elings et al. | 73/105 X |
| 5,423,223 | 6/1995 | Weinstock | 324/209 X |

FOREIGN PATENT DOCUMENTS

| | | |
|---|---|---|
| 2417525 | 10/1975 | United Kingdom . |
| 4342100 | 7/1995 | United Kingdom . |

*Primary Examiner*—Gerard Strecker
*Attorney, Agent, or Firm*—Loeb & Loeb LLP

[57] ABSTRACT

To provide an effective method of nondestructively and easily judging plasticization of steel used in a real construction. A magnetic sensor 10 is made to scan along the surface of steel to detect a magnetic field caused by a magnetic anisotropy induced by plastic deformation of the steel, and the existence and position of the plasticization is judged from the state of distribution of the magnetic field. As a magnetic sensor, a differential type one comprised of detection coils 10a and 10b, the winding directions of which are opposite to each other, is used to compensate a magnetic field intrinsic to the steel.

10 Claims, 6 Drawing Sheets

F I G. 1
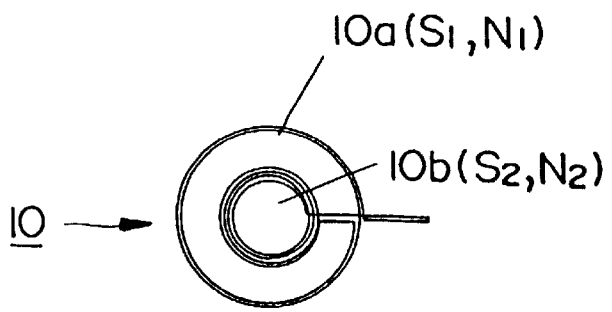
F I G. 2
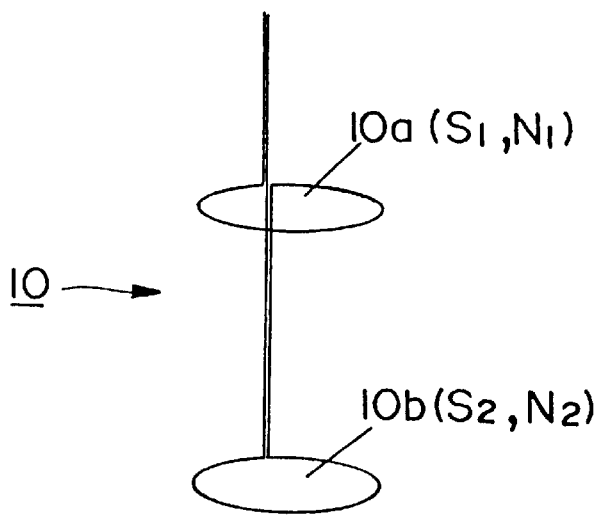
F I G. 3
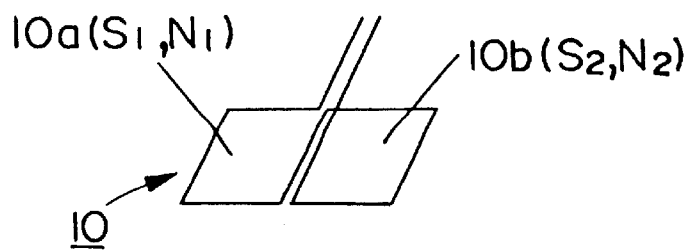

MAGNETIC CONTOUR MAP

DEFORMATION BEHAVIOR GRAPH
OF STEEL

VIEW OF LUDERS BAND DEVELOPMENT

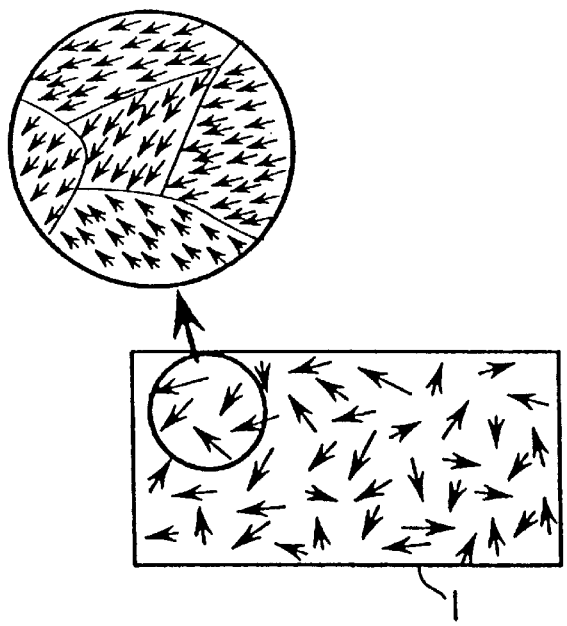
FIG. 12
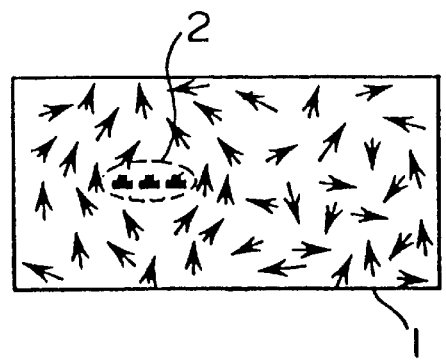
FIG. 13
FIG. 14
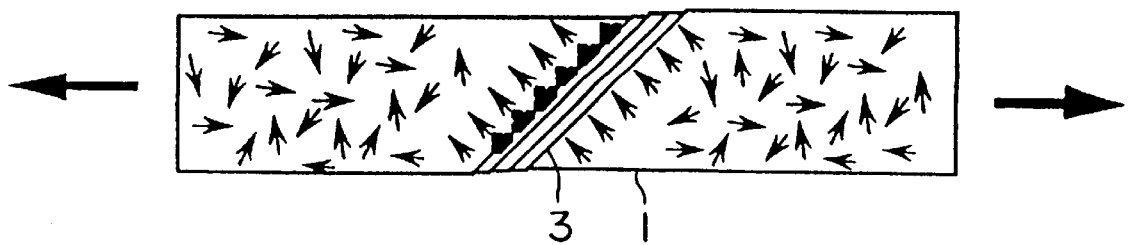

METHOD OF DETECTING PLASTIC DEFORMATION IN STEEL USING A DIFFERENTIAL TYPE MAGNETIC FIELD SENSOR

BACKGROUND OF THE INVENTION

The present invention relates to a method of judging plasticization of steel.

When steel such as steel frames used in a construction as a structural body is given an overload exceeding a yield point, plastic deformation is caused. When the plastic deformation is large, it is possible to know the plasticization of the steel through macroscopic observation or dimensional measurement. However, when the plastic deformation is small, since the amount of deformation of the structure is small, or the plastic deformation is concealed by interior materials or fireproof covering materials covering the steel (steel frame), it is difficult to know the existence of the plastic deformation.

In a construction having suffered damages by a big earthquake, it is important to judge whether the structural material was deformed within the range of elastic deformation, or whether it was given a load exceeding the yield point and was plasticized, when considering the continuous usage of the construction and such measures as necessity of reinforcement. However, there was conventionally only a method of indirect judgement from observation of a deformed state of the construction or observation of damages of interior and exterior materials, that is, there were no effective and suitable technical methods which could directly measure the plasticization of the construction.

Incidentally, as metallurgical methods of judging the plasticization of steel, there are known methods in which the constitution of steel is observed to observe dislocations or slip lines generated in accordance with the plasticization, and the surface of the steel is oxidized(etched) to macroscopically observe a distorted hardened region. However, in order to observe the constitution, it is necessary to pick a sample for observation from the steel and to grind the surface. In the case of observation through etching, after heating the steel to a temperature of 250–300° C., it is necessary to conduct etching by a corrosive liquid. Accordingly, although both methods can be applied to a small test piece in a laboratory, both are difficult to be applied to a real construction. Further, there has been investigated a method in which a sample is arranged in a detection coil, an alternating voltage is applied to the coil, and the characteristics of alternate current magnetization is detected, whereby the plasticization of the sample is judged (for example, see Japanese Patent Unexamined Application No. HEI 6-109412). However, also in this case, it is impossible to apply the method to a real construction like the above described metallurgical methods.

In view of the above circumstances, an object of the present invention is to provide an effective method of judging plasticization of steel used in a real construction in a nondestructive manner and with ease.

SUMMARY OF THE INVENTION

The present invention is characterized by the steps of using a differential type magnetic sensor comprised of detection coils with winding directions opposite to each other; scanning along a surface of steel material with the magnetic sensor; detecting a magnetic field caused by a magnetic anisotropy induced by plastic deformation of the steel material, and judging existence and position of the plasticization from a state of distribution of the magnetic field.

BRIEF DESCRIPTION OF THE DRAWINGS

FIG. 1 is a plan view showing an example of a magnetic sensor used in the present invention.

FIG. 2 is a perspective view showing another example of a magnetic sensor.

FIG. 3 is a perspective view showing still another example of a magnetic sensor.

FIG. 12 is a view schematically showing microscopical magnetic characteristics of the steel in an elastic region.

FIG. 13 is a view schematically showing microscopic magnetic characteristics of the steel in which plasticization is generated.

FIG. 14 is a view schematically showing microscopic magnetic characteristics of the steel in which a Luders band is generated.

EMBODIMENT OF THE INVENTION

Figure 10:
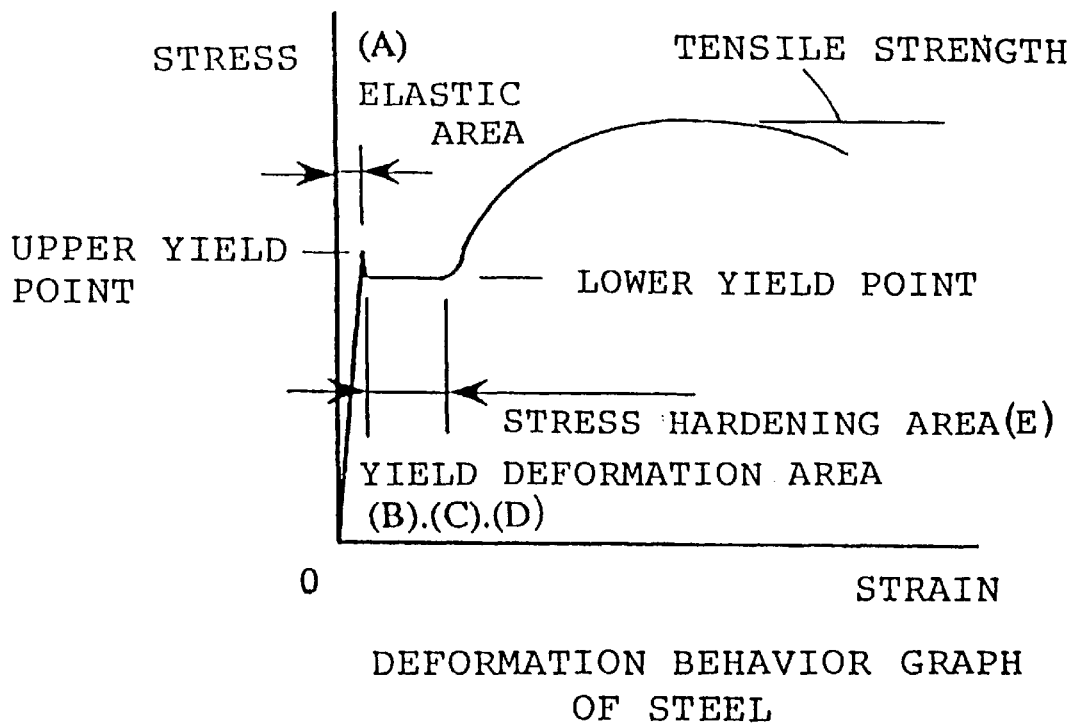
FIG. 10 is a view showing a stress-distortion line of the steel.

Embodiments of the present invention will be described hereinafter. First, with reference to FIGS. 10 to 14, the principle of the present invention will be described. FIG. 10 shows a curve of stress versus distortion of steel, and FIGS. 11 to 14 schematically show the mechanism of plasticization of steel.

The plasticization of steel is caused by generation of dislocations or slip lines in the inside of a crystal. Since the dislocations or slip lines are lattice defects, an uneven stress is generated around them and a magnetic anisotropy induced by the stress is generated. In the present invention, an attention is paid to the magnetic anisotropy generated by plastic deformation, and the existence or position of the plastic deformation is judged by detecting the magnetic field caused by the magnetic anisotropy.

That is, as shown in FIG. 12, steel 1 is microscopically formed of a number of magnetic domains, and a number of magnetic spins directed in the same direction exist in the respective magnetic domains. However, in an elastic region A (FIGS. 10 and 11), the directions of magnetization of the respective magnetic domains are random, so that the steel 1 shows isotropic magnetization characteristics in total.

Figure 11:
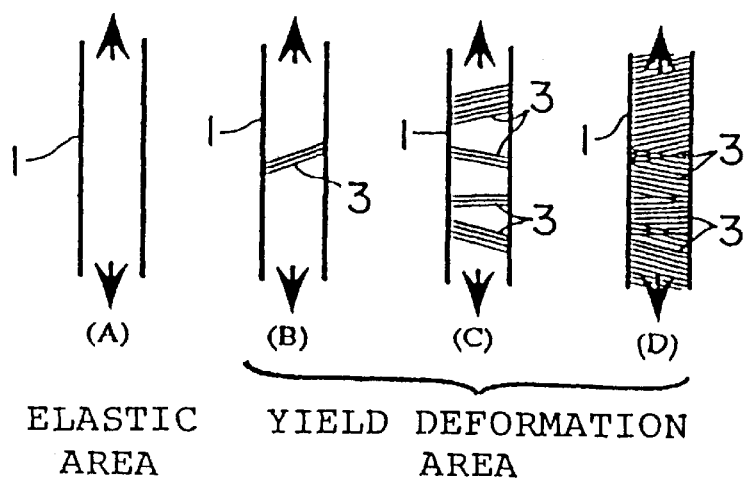
FIG. 11 is a view schematically showing the mechanism of plasticization of the steel and showing the state of generation of Luders band.

When a load near a yield point is applied to the steel 1, as shown in FIG. 13, a dislocation 2 and a slip of a group of dislocations are generated in its constitution. A microscopic stress field is generated around the dislocation 2 or the slip, and in a ferromagnetic substance such as the steel 1, a magnetic anisotropy induced by the stress is generated near the stress field. Further, when a load exceeding a yield point is applied to the steel 1, the steel 1 is not uniformly plastically deformed, but as shown in FIG. 14, inhomogeneous plastic deformation called Luders band 3 is generated. As shown in FIG. 11, such Luders band 3 gradually expands at lower yield point stress in yielding deformation regions B, C, and D. After the Luders band 3 develops into the entire of the steel 1, the state of the steel is put into a distorted hardened region E where the intensity increases as the distortion increases.

Since the Luders band 3 is a portion where slips are gathered, a remarkable magnetic anisotropy is induced in the vicinity thereof. As a result, a magnetic field is formed outside the steel 1. Then, if the magnetic field is detected, the existence and position of the Luders band 3 can be detected, so that plasticization can be judged. However, since the normal steel 1 is ferromagnetic substance, it has also an intrinsic magnetic field, and the magnetic field intrinsic to the steel 1 and the magnetic field caused by the plastic deformation are superimposed outside the steel 1. Accordingly, in order to judge the plasticization, it is necessary to measure only the magnetic field caused by the plastic deformation, that is, it is necessary to compensate the magnetic field intrinsic to the steel 1 to selectively take out only the magnetic field caused by the plastic deformation.

Then, in the present invention, providing that the steel 1 is not magnetized in a specific direction, an attention is paid to a fact that a spatial distribution of the magnetic field intrinsic to the steel 1 is gentle, while a spatial distribution of the magnetic field caused by the plastic deformation causing the Luders band 3 has a large variation since the Luders band 3 is locally generated in the inside of the steel 1. Thus, a differential type magnetic sensor, that is, the magnetic sensor of the type in which a local variation of the magnetic field intensity can be detected with high precision, is used to scan the surface of the steel 1, so that the spontaneous magnetic field near the surface of the steel 1 is obtained and from the state of plane distribution, the existence and position of the Luders band 3 are detected. That is, if the magnetic fields along the surface of the steel 1 are obtained, and the state of plane distribution thereof is expressed by an equal magnetic line diagram, i.e., a contour diagram of magnetic field, at the stages where the Luders band 3 is locally generated (yielding deformation regions B, C, and D), the magnetic field abruptly changes at the portion corresponding to the Luders band 3, whereas at the stages where the Luders band 3 is generated in the entire surface of the steel 1 (distorted hardened region E), the plane distribution of the magnetic field has a small variation, whereby the existence, position and degree of plasticization can be judged.

An embodiment of the present invention based on the above-mentioned principle will be described concretely. FIG. 1 shows a magnetic sensor 10 used in this embodiment. This magnetic sensor 10 is of a differential type and includes double detection coils 10a and 10b. The respective detection coils 10a and 10b have a minute area less than about 1 mm diameter, are arranged concentrically and on the same plane, the numbers of windings being adjusted so that the total areas (the total area for a coil is the product of the area of each winding and the number of windings) for the two coils are equal to each other, and the directions of the windings being opposite to each other. In this embodiment, when the areas of the detection coils 10a and 10b are S1 and S2, and the numbers of winding are N1 and N2, the numbers and areas are set so as to satisfy the equation of S1×N1=S2×N2. With the differential type magnetic sensor 10 comprised of the detection coils 10a and 10b with such a minute area, a locally changing magnetic flux can be detected with high precision, and a magnetic flux from a remote magnetic source and a magnetic flux with a gentle variation can be compensated. As the magnetic sensor 10, it is preferable to adopt a high sensibility magnetic flux sensor using, for example, a superconductive quantum interference element, and an area of detected portion of magnetic field can be sufficiently made small so that spatial resolving power can be sufficiently heightened thereby. The detection coils 10a and 10b of the magnetic sensor 10 are not limited to the above described circular ones which are concentrically arranged on the same plane. For example, as shown in FIG. 2, detection coils 10a and 10b may be arranged with an interval in a vertical direction. Alternatively, as shown in FIG. 3, rectangular or polygonal detection coils 10a and 10b may be arranged side by side.

Figure 4:
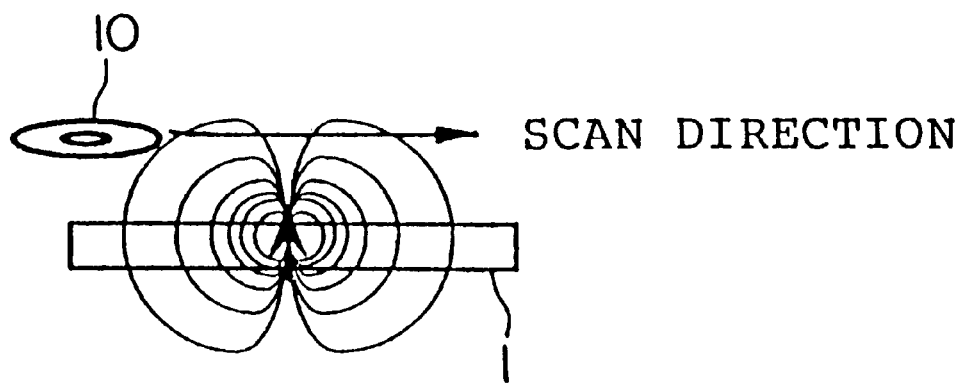
FIG. 4 is a view showing a procedure of the present invention, and schematically showing the state in which a magnetic sensor scans the steel in one-dimension.
Figure 5:
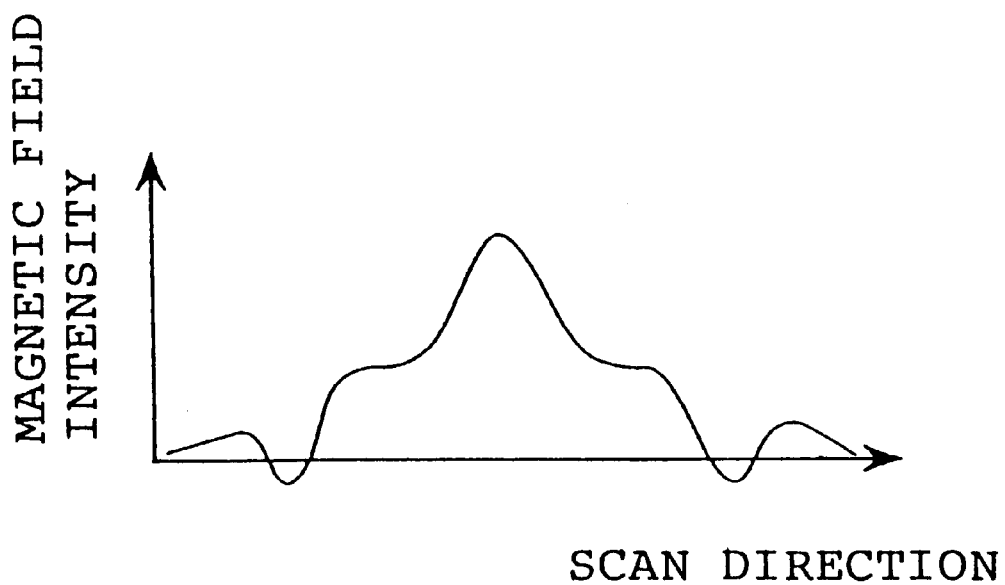
FIG. 5 is a view schematically showing the one-dimensional distribution of magnetic field obtained by the scan.
Figure 6:
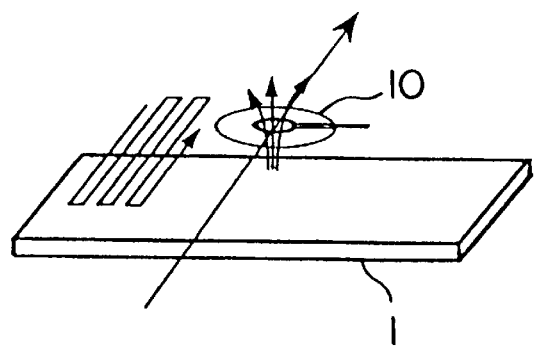
FIG. 6 is a view schematically showing the state in which the magnetic sensor scans along the surface of the steel in a plane.
Figure 7:
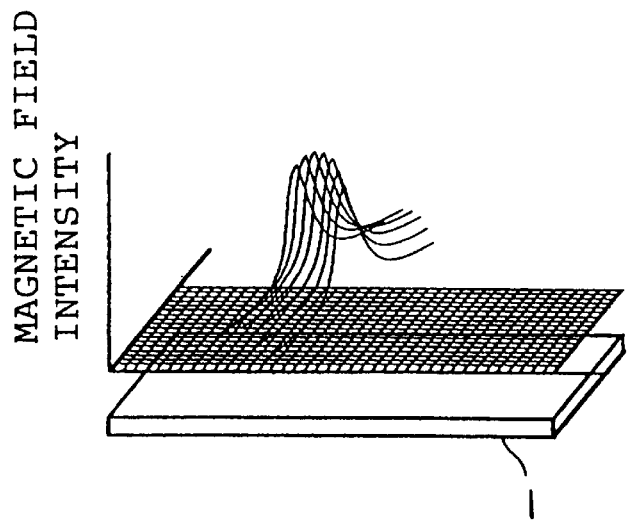
FIG. 7 is a view schematically showing the plane distribution of magnetic field intensity obtained by the scan.
Figure 8:
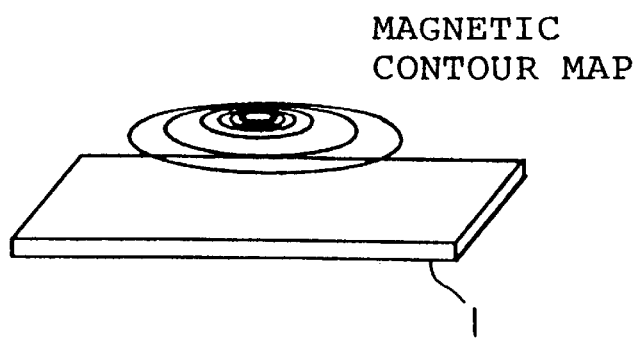
FIG. 8 is a view schematically showing a magnetic contour diagram based on the distribution of the magnetic field intensity.
Figure 9:
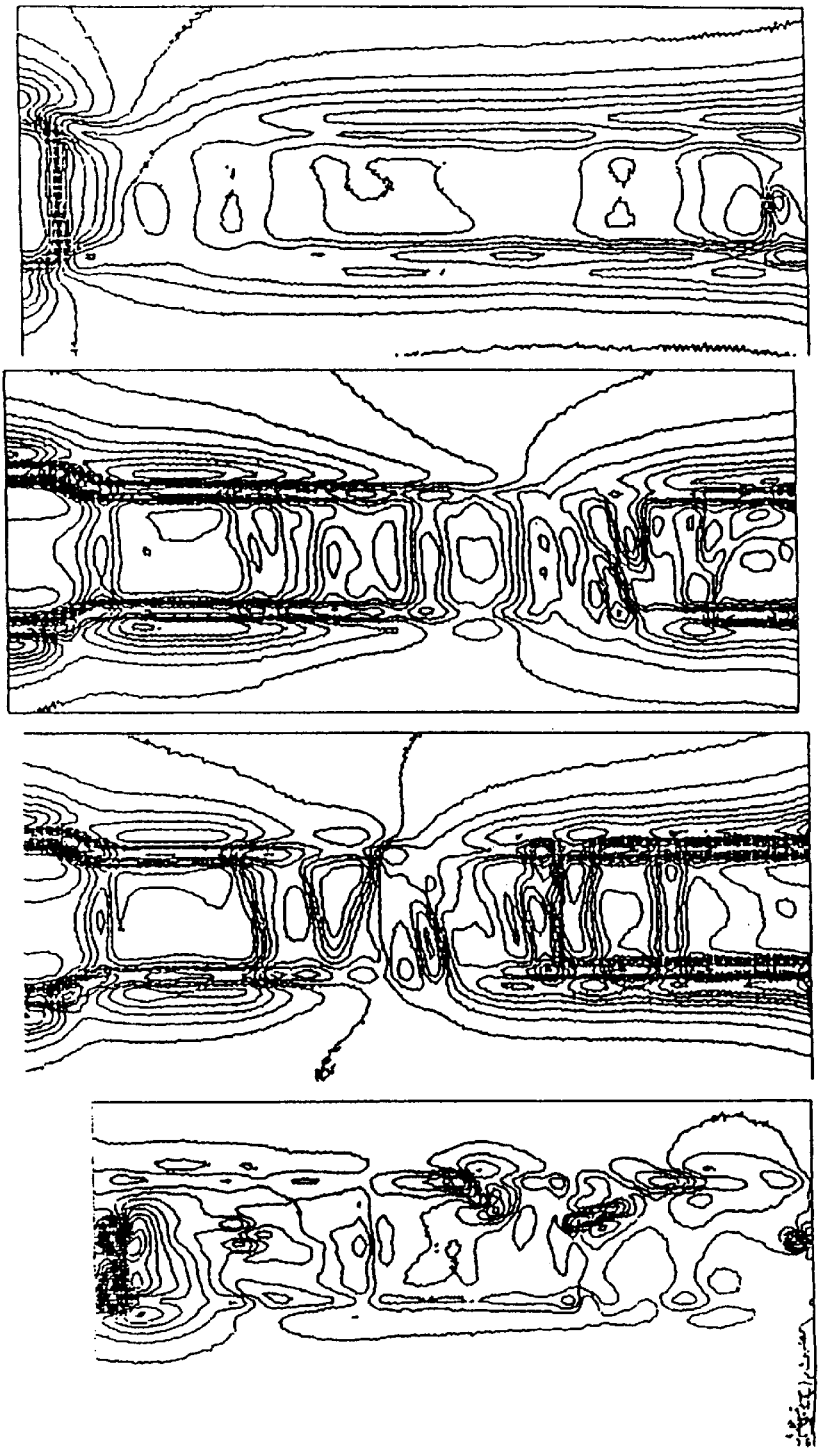
FIG. 9 is a view showing examples of magnetic contour diagrams based on actual distributions of magnetic field intensities.

As shown in FIG. 4, since the magnetic field generated by magnetization in the inside of the steel 1 as an objective sample is distributed to the outside of the steel 1, when the above-mentioned magnetic sensor 10 is arranged near the surface of the steel 1, the magnetic sensor detects the vertical component of the magnetic field. When the magnetic sensor 10 is made to scan in parallel to the surface of the steel, a one-dimensional distribution of magnetic field intensity as shown in FIG. 5 is obtained. Further, as shown in FIG. 6, when the magnetic sensor 10 is made to scan along a rectangular wave-like path over the entire surface of the steel, a plane distribution of magnetic field intensity as shown in FIG. 7 is obtained. Then, scanning points are set on the respective scanning lines in accordance with a sampling frequency, the magnetic field intensity at each of the scanning points is converted into digital values through an A/D convertor, and points among the respective scanning points equal in magnetic field intensity are joined to prepare an equal magnetic line diagram as shown in FIG. 8. FIG. 9(a) shows an example of the equal magnetic line diagram in an elastic region based on actual data. It should be noted that the invention is not limited to the above described case in which a magnetic field vertical to the steel is measured, but a magnetic field parallel to the surface of the steel may be measured. However, in the case where the magnetic field in the vertical direction is measured, since the directionality of the magnetic field can be neglected, it is more preferable.

If the steel 1 is subject to plastic deformation to generate the magnetic anisotropy in the inside thereof, the distribution of magnetic field caused by the magnetic anisotropy is generated outside the steel 1, which is reflected to the equal magnetic line diagram obtained as described above Then, by analyzing the diagram, it is possible to judge the plasticization. That is, as described above, when the Luders band 3 is generated in the yielding deformation regions B, C, and D in the steel 1, the magnetic field abruptly changes at that position, while at the stage where the state of the steel 1 reaches the distorted hardened region E so that the Luders band 3 is generated over the entire surface of the steel 1, the plane distribution of the magnetic field has a small variation. From the above, it is possible to judge the existence and position of the plasticization, as well as whether the plasticization reaches the distorted hardened region E from the yielding deformation region D, and the like. FIGS. 9(b) and (c) show examples of equal magnetic line diagrams in the yielding deformation regions based on actual data, and FIG.

9(d) shows an example of equal magnetic line diagram in the distorted hardened region.

According to the above-described method, by only making the magnetic sensor 10 scan along the surface of the steel 1 of an object to be inspected in a noncontact manner, the intrinsic magnetic field near the surface of the steel 1 is measured and the plasticization can be judged from the state of the plane distribution of the magnetic field. Accordingly, the plasticization of the steel 1 can be judged in a nondestructive manner, and the invention can be easily applied to a real construction without any trouble thereby. Especially, in the above-mentioned method, by using the differential type magnetic sensor 10, the magnetic field having a gentle spatial distribution and intrinsic to the steel is compensated, and only steep magnetic field change caused by the plasticization can be effectively detected. Also, using the minute size magnetic sensor 10 superior in spatial resolution power enables the measurement of a local magnetic field caused by the plasticization with high precision.

As described above, according to the present invention, the differential type magnetic sensor is made to scan along the surface of the steel so that the magnetic field caused by the magnetic anisotropy induced by the plastic deformation of the steel is detected and the existence and position of the plasticization is judged from the state of distribution of the magnetic field. Accordingly, without breaking or damaging the steel of an object to be inspected, and without requiring labor such as a specific pretreatment or application of a voltage to a sample, it is possible to effectively judge the existence, position and degree of the plasticization of the steel material. Therefore, the invention can be applied to a real construction. As a result, it becomes possible to judge the existence of minute plastic deformation of a real construction which can not be judged by macroscopic observation or dimensional measurement, being extremely effective.

What is claimed is:

1. A method for detecting plastic deformation in a piece of steel comprising:

scanning with a differential type magnetic sensor along a surface of the steel;

detecting a local variation of a magnetic field using the differential type magnetic sensor, the magnetic field being caused by a magnetic anisotropy induced by plastic deformation in the steel;

producing a representation of a distribution of the detected local variation of the magnetic field along the surface of the steel; and determining the existence and locations of the plastic deformation based on the representation.

2. The method of claim 1, wherein the differential type magnetic sensor comprises two detection coils coupled together, the total areas of the two coils being the same and the winding directions of the two coils being the opposite of each other.

3. The method of claim 2, wherein the two detection coils are located in substantially the same plane.

4. The method of claim 3, wherein the two detection coils comprise concentric circles.

5. The method of claim 3, wherein the two detection coils are displaced laterally within the plane in which they are located.

6. The method of claim 3, wherein the plane of the detector coils is substantially parallel to the surface of the steel.

7. The method of claim 2, wherein the differential type magnetic sensor comprises two detection coils located substantially in planes parallel to each other.

8. The method of claim 6, wherein the determination of the existence and locations of the plastic deformation is based on the degree of spatial variation of the magnetic field.

9. The method of claim 8, wherein plastic deformation is determined to exist adjacent locations where the magnetic field has a substantially higher degree of spatial variation than other locations along the surface of the steel.

10. The method of claim 1, wherein the representation of the distribution of the detected magnetic field is a contour diagram of the magnetic field.

* * * * *